US010082517B2

(12) United States Patent
Ackermann et al.

(10) Patent No.: US 10,082,517 B2
(45) Date of Patent: Sep. 25, 2018

(54) REAGENT MANAGEMENT SYSTEM

(71) Applicant: Roche Diagnostics Operations, Inc., Indianapolis, IN (US)

(72) Inventors: Friedrich Ackermann, Heidelberg (DE); Andreas Calatzis, Rotkreuz (CH); Rik Harbers, Cham (CH); Roland Hutter, Zug (CH); Jean-Pierre Bolliger, Buchrain (CH); Theresa Kitcoff, Leesburg, VA (US); Patrick Sascha Labud, Zurich (CH)

(73) Assignee: Roche Diagnostics Operations, Inc.

( * ) Notice: Subject to any disclaimer, the term of this patent is extended or adjusted under 35 U.S.C. 154(b) by 0 days.

(21) Appl. No.: 15/084,663

(22) Filed: Mar. 30, 2016

(65) Prior Publication Data

US 2016/0299164 A1 Oct. 13, 2016

(30) Foreign Application Priority Data

Apr. 7, 2015 (EP) .................................... 15162612

(51) Int. Cl.
*G01N 35/00* (2006.01)
*B01L 9/00* (2006.01)
(Continued)

(52) U.S. Cl.
CPC .......... *G01N 35/00663* (2013.01); *B01L 9/00* (2013.01); *G01N 35/0092* (2013.01);
(Continued)

(58) Field of Classification Search
CPC ......... G01N 35/00663; G01N 35/1002; G01N 35/1016; G01N 2035/0094;
(Continued)

(56) References Cited

U.S. PATENT DOCUMENTS

2010/0322822 A1 12/2010 Fritchie et al.
2011/0151504 A1 6/2011 Avantsa et al.
(Continued)

FOREIGN PATENT DOCUMENTS

EP 2224247 A2 9/2010
JP 2014-020885 A 2/2014
(Continued)

OTHER PUBLICATIONS

King, Lindsay E. et al., Ligand Binding Assay Critical Reagents and Their Stability: Recommendations and Best Practices from the Global Bioanalysis Consortium Harmonization Team, The AAPS Journal, 2014, pp. 504-515, vol. 16, No. 3.
(Continued)

*Primary Examiner* — Christopher Adam Hixson
(74) *Attorney, Agent, or Firm* — Roche Diagnostics Operations, Inc.

(57) ABSTRACT

A reagent management system is disclosed comprising a reagent container section for receiving reagent containers and a reagent reconstitution device for reconstituting dry, or lyophilized, reagents or concentrated reagents in reagent containers in order to carry out in-vitro diagnostic tests with the reconstituted reagents. A controller is programmed to instruct the reagent reconstitution device to automatically reconstitute an initial volume of a selected reagent type in reagent containers. The initial volume is calculated based on an open container stability time (OCS) of the reconstituted reagent type for each reagent container and on a number of tests to be carried out within the OCS of the reconstituted reagent type. A reagent container for use by the reagent management system and methods of automatically reconstituting a dry, or lyophilized reagent, or a concentrated liquid reagent in a reagent container to carry out an in-vitro diagnostic test with the reagent are disclosed.

10 Claims, 8 Drawing Sheets

(51) Int. Cl.
*G01N 35/10* (2006.01)
*G01N 35/04* (2006.01)

(52) U.S. Cl.
CPC . *G01N 35/00693* (2013.01); *G01N 35/00722* (2013.01); *G01N 35/04* (2013.01); *G01N 35/1002* (2013.01); *G01N 35/1009* (2013.01); *B01L 2200/025* (2013.01); *G01N 35/1016* (2013.01); *G01N 35/1079* (2013.01); *G01N 2035/0094* (2013.01); *G01N 2035/00425* (2013.01); *G01N 2035/00673* (2013.01); *G01N 2035/00891* (2013.01); *G01N 2035/0406* (2013.01); *G01N 2035/1025* (2013.01)

(58) Field of Classification Search
CPC . G01N 2035/1025; G01N 2035/00673; G01N 35/04; G01N 35/1009; G01N 35/0092; G01N 35/00722; G01N 35/00693; G01N 35/1079; G01N 2035/0406; G01N 2035/00425; G01N 2035/00891; B01L 9/00; B01L 2200/025
See application file for complete search history.

(56) References Cited

U.S. PATENT DOCUMENTS

| 2012/0241045 | A1* | 9/2012 | Aouad | B01F 1/0038 141/83 |
| 2014/0048556 | A1* | 2/2014 | Pearcy | A61M 5/284 222/1 |
| 2015/0251840 | A1* | 9/2015 | Kuehn | B01L 3/0227 222/23 |

FOREIGN PATENT DOCUMENTS

| JP | 2015-021943 A | 2/2015 |
| WO | 2008/012596 A2 | 1/2008 |
| WO | 2014/153193 A2 | 9/2014 |

OTHER PUBLICATIONS

Pihl, Susanne, Presenter on behalf of EBF TT-47, EBF recommendation on practical management of critical reagents for ligand-binding assays, EBF Open Symposium, 2014, 22 pages.

* cited by examiner

REAGENT MANAGEMENT SYSTEM

CROSS-REFERENCE TO RELATED APPLICATIONS

This application claims priority to EP 15162612.4, filed Apr. 7, 2015, which is hereby incorporated by reference.

BACKGROUND

The present disclosure relates to a reagent management system, a method for automatically reconstituting reagents in order to carry out in-vitro diagnostic tests, and a reagent container holder to be used with the reagent management system.

In analytical laboratories, in particular, in-vitro diagnostic laboratories, a multitude of analyses on biological samples are executed in order to determine physiological and biochemical states of patients, which can be indicative of a disease, nutrition habits, drug effectiveness, organ function and the like.

Sample processing throughput, i.e., the number of biological samples analyzed per hour, as well as the number of different tests that can be carried out, are generally important. For laboratories handling thousands of samples each day, a small delay for each individual sample makes a substantial difference in terms of overall laboratory efficiency.

In order to meet this demand, optimal hardware design and efficient workflow planning are required in order to optimize the use of functional resources and maximize throughput. In particular, an automated system for in-vitro diagnostic analysis may be required to execute a large number of complex scheduled process operations, involving the repeated use of the same functional resources, possibly for different uses at different times of the process. Also, it is frequent that different tests require different test conditions, e.g., different reaction times, different types of reagents, different volumes, different detection times, and the like. The system should be also sufficiently flexible to new or changed user requests and be able to respond quickly to unpredicted situations like errors, failures and other unusual situations in the performance of a test.

Most diagnostics tests can be carried out with ready-to-use liquid reagents that have sufficiently long shelf-life in the liquid form, particularly in closed reagent containers. Many also have a sufficiently long open container stability under certain conditions, e.g., under refrigeration. On the other hand, some reagent types required to carry out other in-vitro diagnostic tests, such as some coagulation tests, are not stable in the liquid form.

Many of the coagulation reagents and controls that are required for coagulation testing come in a lyophilized formulation. Lyophilization refers to the process of freeze drying the liquid reagent which removes the liquid component and leaves a dry powder behind. As clot based coagulation testing requires the key components (e.g., tissue factor in the thromboplastin reagent) to be biologically active, lyophilization is necessary to preserve this function. In the lyophilized form, the tissue factor is preserved thereby giving the reagents a long shelf life. Before use in a test, the reagents need to be reconstituted with the exact amount of diluent (liquid) as prescribed in the package insert. However, it should be noted that once converted back into a liquid, the reagents can only be used for a very limited period. This limited period is referred to as the 'open container stability time'. Whilst the shelf lives for closed containers are long (measured in months or years), the open container stability time of reagents and controls is typically short (measured in hours or days) and varies from reagent to reagent.

The lack of adherence to the storage conditions and times is a major source of error in the coagulation laboratory. Also, as these types of reagents are expensive they have to be used sparingly and with care.

Normally, lyophilized coagulation reagents are reconstituted manually just before use or, for example, at the beginning of the day based on an expected number of tests in the same day to be carried with those specific reagent types. This is not only time consuming and prone to errors, but also a real bottleneck with respect to throughput and workflow optimization, especially if the total volume of reconstituted reagents needed is underestimated and additional reagents have to be reconstituted. On the other hand, if the total volume of reconstituted reagents needed is overestimated, pricey and valuable reagents can be wasted once they have been reconstituted.

Therefore, there is a need for an automated reagent management system which provides higher processing throughput and workflow efficiency as well as optimal use of reagents, thereby ensuring reagent availability when needed and minimizing the risk of wasting valuable reagents through the use of a programmed controller that automatically selects the right reagent containers to be reconstituted at the right time and instructs an automatic reconstitution device to perform a series of reconstitution steps.

SUMMARY

According to the present disclosure, a reagent management system, a reagent container for use by the reagent management system, and methods of automatically reconstituting a dry, or lyophilized reagent, or a concentrated liquid reagent in a reagent container to carry out an in-vitro diagnostic test with the reagent are presented. The reagent management system can comprise a reagent container section for receiving reagent containers, a reagent reconstitution device for reconstituting dry, or lyophilized, reagents or concentrated liquid reagents provided in the reagent containers in order to carry out in-vitro diagnostic tests with the reconstituted reagents, and a controller programmed to instruct the reagent reconstitution device to automatically reconstitute a volume of a selected reagent type in one or more reagent containers. The controller can calculate the volume based at least on an open container stability time (OCS) of the reconstituted reagent type for each reagent container and on a number of tests that can be carried out within the open container stability time (OCS) of the reconstituted reagent type.

Accordingly, it is a feature of the embodiments of the present disclosure to provide an automated reagent management system which provides higher processing throughput and workflow efficiency as well as optimal use of reagents, thereby ensuring reagent availability when needed and minimizing the risk of wasting valuable reagents through the use of a programmed controller that automatically selects the right reagent containers to be reconstituted at the right time and instructs an automatic reconstitution device to perform a series of reconstitution steps. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
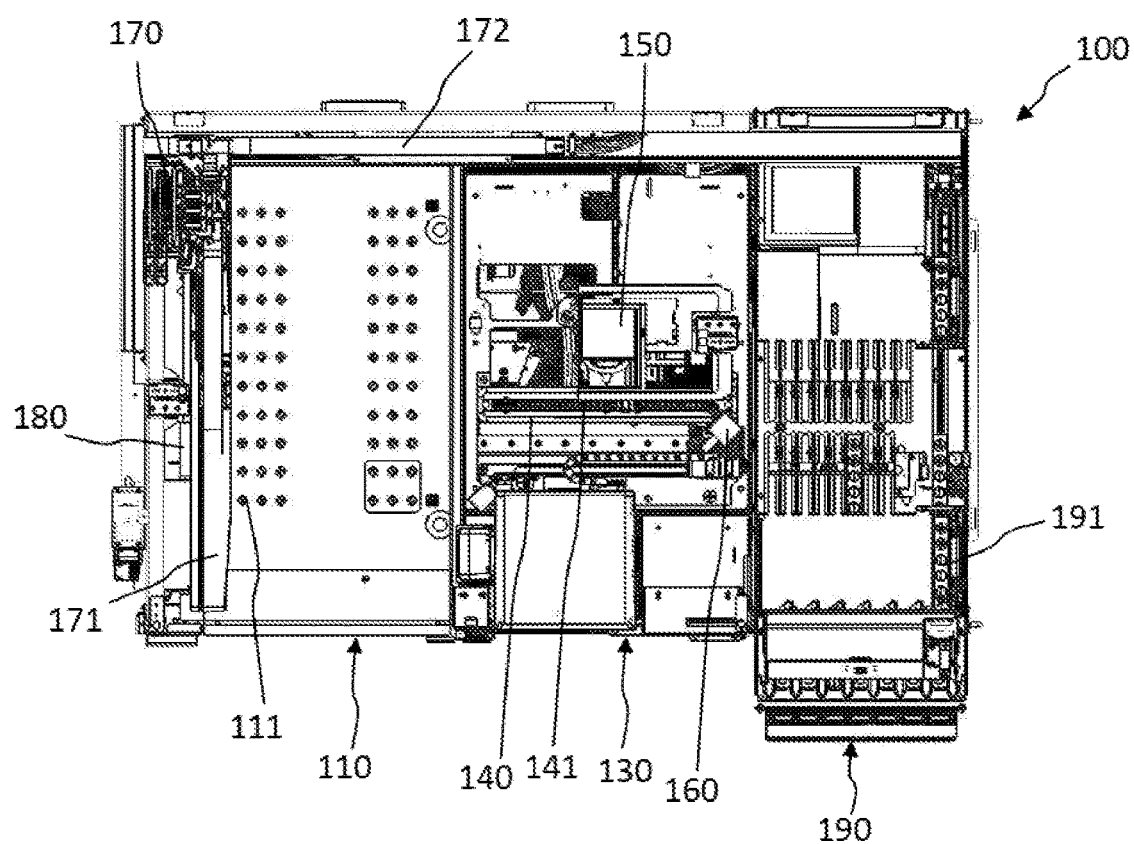
FIG. 1 illustrates a top view of a system for in-vitro diagnostics (parts and cover removed for clarity) comprising a reagent management system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A "reagent management system" can be an automatic laboratory system for receiving reagent containers, managing reagent containers, and providing reagents for carrying out in-vitro diagnostic tests. The reagent management system can be a module or unit integrated in a larger system for in-vitro diagnostics, and possibly sharing functional units with the rest of the in-vitro diagnostics system. Alternatively, the reagent management system may be a stand-alone device communicating with a larger IT system for in-vitro diagnostics.

A "system for in-vitro diagnostics" can be an apparatus, e.g., a laboratory automated instrument dedicated to the analysis of samples or to the preparation of samples for in-vitro diagnostics (analytical or pre-analytical apparatus) and involving the use of reagents. Examples of such analytical apparatuses are clinical chemistry analyzers, coagulation analyzers, immunochemistry analyzers, hematology analyzers, urine analyzers and nucleic acid analyzers that are used for the qualitative and/or quantitative detection of analytes present in the samples, to detect the result of chemical or biological reactions and/or to monitor the progress of chemical or biological reactions.

According to an embodiment, the analytical apparatus can be a coagulation analyzer for carrying out coagulation tests and involving the use of coagulation reagents.

The analytical apparatus may comprise functional units for pipetting and/or mixing of samples and/or reagents and/or for carrying out dedicated workflow tasks, e.g., loading and/or unloading and/or transporting and/or storing sample tubes or racks comprising sample tubes, loading and/or unloading and/or transporting and/or storing reagent containers or cassettes, loading and/or unloading and/or transporting and/or storing and/or washing reaction vessels, e.g., cuvettes, loading and/or unloading and/or transporting and/or storing pipette tips or tip racks, reading and/or writing information, e.g. contained in barcodes or RFID tags, washing pipette tips or needles or reaction vessels, e.g. cuvettes, mixing paddles, mixing of samples with other liquid, e.g., reagents, solvents, diluents, buffers, decapping, recapping, pipetting, aliquoting, centrifuging, and so on. It may comprise a consumable feeding unit, e.g., for feeding reaction vessels. The analytical apparatus can further comprise a particular detection unit and follow a particular workflow, e.g., execute a number of processing steps, which can be optimized for certain types of analysis, e.g., coagulation.

The analytical apparatus may have different configurations according to the need and/or according to the desired laboratory workflow. Additional configurations may be obtained by coupling a plurality of apparatuses together and/or adding modules. A "module" can be a work cell, typically smaller in size and weight than an entire analytical apparatus, which can have an auxiliary function to the analytical function of an analytical apparatus and can work only together with an analytical apparatus. In particular, a module can be configured to cooperate with one or more analytical apparatuses. In some embodiments, the disclosed reagent management system may be one of such modules.

A "reagent" can be a substance used for treatment of a sample in order e.g. for a reaction to occur, or to enable detection of a physical parameter of the sample or analyte contained in the sample. In particular, a reagent can be a substance that is or comprises a reactant, typically a compound or agent capable e.g., of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, and the like. According to certain embodiments, the reagents can be dry or lyophilized reagents. According to certain embodiments, the reagents can be coagulation reagents. In particular, some coagulation reagents can be provided in lyophilized form, e.g., thromboplastin reagents used for Prothrombin Time (PT) testing, in order to increase their shelf life. Some reagents can be provided in liquid form, including some coagulation reagents. For example, in contrast to the PT reagents, the Activated Partial Thromboplastin Time (APTT) reagent may come as a liquid formulation. This can be because the activator which initiates the clotting reaction, unlike the thromboplastin reagent, is an inert substance that has no inherent biological function. It is the charged nature of this substance that can react with clotting factor XII (the starting point of the APTT) rather than enzymatic activity. Consequently, the reagent can be stable as a liquid, although the shelf life can somewhat be shorter than the lyophilized reagents. Once opened, the same open container stability issues can apply as exposure to air can initiate a slow decline in the stability of the product. In contrast, reagents such as calcium chloride can be inert chemicals; hence they can have both a long shelf life and a long stability even after opening.

Some reagents requiring relatively larger volumes of liquid for testing, e.g., used for carrying out some hematology tests, can come as concentrated liquid formulations in closed reagent containers and have to be diluted before use in a test. So storing and handling, including transporting and moving, of larger volumes and heavier containers can be prevented by diluting the concentrated liquid reagents on-site before use. Once the reagent container is opened, the same open container stability issues can apply as exposure to air can initiate a slow decline in the stability of the product. The disclosed reagent management system can be suitable also for automatically diluting concentrated liquid reagents.

According to certain embodiments, the reagents can thus be concentrated liquid reagents. According to certain embodiments, the reagents can be hematology reagents. According to an embodiment, the analytical apparatus can be a hematology analyzer for carrying out hematology tests and involving the use of hematology reagents.

A "reagent type" can be a reagent dedicated to carry out a particular test type, e.g., a PT test, an APTT test, and the like. Thus, typically, different reagent types can be dedicated to different tests although sometimes the same reagent type may be employed in different tests.

The term "shelf life" can refer to a period of time during which a reagent can be usable after it has been manufactured and has been maintained at specified storage conditions in its sealed reagent container. The shelf life can be indicated as expiry date, beyond which the reagent can no longer be usable. The shelf life can typically be in the range of months or years for most reagents. The shelf life can be encoded in an information carrying tag, e.g. a barcode or RFID tag on the reagent container or reagent container holder. Also, or in alternative, the shelf life can be readable as text on the reagent container or reagent container holder and/or specified in a definition file related to the reagent container or reagent container holder (master data). The shelf life can typically be linked to a reagent lot so that reagent containers or reagent container holders of the same manufacturing lot can have the same expiration date. For a reagent container holder holding a plurality of reagent containers, the shelf life can typically refer to the shelf life of the reagent container holder as a whole, which can typically refer to the shelf life of the reagent type with the shortest shelf life in the reagent container holder in case the reagent containers are different and have different shelf lives. However, individual expiration dates may be assigned to individual reagent containers in the same reagent container holder and specified in the definition file. Shelf life can be reduced, for example, by storage at higher temperatures or due to exposure to light. It can be the case that a particular reagent can have one shelf life for storage in a freezer, but also can have a shorter shelf life for storage at room temperature.

The term "open container stability" can refer to a period of time during which a reagent can be usable after its reagent container has been opened for the first time after manufacture. The open container stability time can typically be in the range of hours or days. The open container stability can be recorded in the reagent container definition file and can be individually assigned to each opened reagent container, as each reagent container can be opened independently from others. This can apply even in case of reagent container holders with a plurality of reagent containers.

A "reagent container" can have a closed container having an inner space adapted for containing reagents isolated from the environment in order to extend their shelf life as long as possible. Depending on the reagent type, the reagent container may comprise a body made e.g., of a plastic polymeric material or glass, and a closure sealing an opening of the reagent container body. The closure may be an openable closure, e.g. removable from the opening, e.g., by screwing or pulling, or pivotable with respect to the opening or to a base portion of the closure attached to the opening. The closure may comprise an additional seal. According to an embodiment, the body can be made of glass and the closure can be made of, or comprise, an elastomeric pierceable material or can be replaceable by a closure made of, or comprising, an elastomeric pierceable material. The reagent container may have any shape, e.g., the shape of a cylindrical bottle or vial, e.g., with a tapering neck towards the opening, and may have any capacity, but more typically in the range of a few milliliters to several milliliters.

According to an embodiment, the reagent container can be a flow-through cartridge comprising a channel, chamber or the like between an inlet and an outlet, with dry or lyophilized reagent sealed therein. Such flow-through cartridges can often have a capacity measured in microliters.

The reagent container may have, however, any other suitable shape including a pouch shape, a sealed bag or the like.

A "reagent container holder" can be a carrier suitable to hold, handle, store and transport one or more reagent containers. The reagent container holder may be embodied, for example, as a reagent pack, configured e.g. like a cassette, comprising one or more reagent containers, or as an adapter configured like a rack comprising one or more reagent container receiving positions for receiving one or more reagent containers, possibly of different sizes, capacities and shapes. According to an embodiment, the reagent container holder can comprise a lock-in mechanism enabling stable holding/fixing of the reagent containers, including, for example, during handling or agitation of the reagent container holder. The lock-in mechanism may be a mechanical element that can assume at least two positions, one open position enabling insertion or removal of a reagent container from a reagent container receiving position, configured, for example, as a recess, cavity or the like, and one locked position respectively preventing removal of the reagent container. The mechanical element may be resilient, or comprise a resilient feature, that can maintain the mechanical element in the locked position until manually or automatically biased into the open position. According to an embodiment, the reagent container holder can comprise at least two different parts and, in particular, a base part with one or more reagent container receiving positions and a cover part to lock reagent containers between the base part and the cover part. The cover part may comprise access ports, e.g. holes, in order to access the reagent containers in the reagent container holder without opening the cover. According to an embodiment, the cover can be an attachable strip, tape or foil-like cover, e.g. adhesive that closes one or more reagent containers in one or more reagent container receiving positions. In particular, the cover may be pierceable for accessing the reagent containers closed between the base part and the cover. Alternatively, a cover for each reagent container receiving position may be used that can also provide information, e.g., via a barcode, 2D code, or alphanumeric code, with respect to a reagent container in that reagent container position. The code may be positioned, for example, in a manner that if it can be readable can indicate presence of a reagent container in the respective reagent container position and if it cannot be readable can indicate absence of a reagent container in the same position or, for example, that a reagent container has already been opened, e.g., following removal or damage of the cover or code on the cover in order to make the reagent container accessible.

The reagent management system can comprise a reagent container section for receiving reagent containers. A "reagent container section" can be a dedicated and limited area, or space, of the reagent management system adapted to receive reagent containers, either directly or in reagent container holders. In particular, the reagent container section may be embodied as a compartment comprising a plurality of receptacles, slots or the like acting as receiving positions for accommodating reagent containers or reagent container holders. A receiving position of the reagent container section may thus have the function of a reagent container holder or of a reagent container holder holder. According to an embodiment, the receiving positions can be adapted to fit a reagent container holder of standard size, whereas the size, capacity and shape of reagent containers in the same reagent container holder, or in different reagent container holders, may vary. The compartment may be refrigerated in order to extend the shelf life and/or the open container stability time of the reagents contained in it. The receiving positions may be arranged in a compact manner next to each other in any format, e.g. in a linear or circumferential manner, in a static or conveying manner, e.g. arranged in a rotor-like conveyor or in a fixed position of a static holding block. According to an embodiment, the reagent container section can comprise a housing comprising a plurality of linearly arranged receiving positions on at least two levels above each other. The receiving positions may have different functions. A receiving position may be for example a storage position or a pipetting position or a reagent container opening position, e.g., a piercing position. The reagent container section may comprise other receiving positions such as a liquid dispensing position and a reagent container agitating position. According to an embodiment, the housing can comprise at least one inlet/outlet interface, such as e.g., a port, door, drawer or the like comprising one or more inlet/outlet receiving positions for introducing and removing reagent containers or reagent container holders from the reagent container section. The reagent containers may be accessible from the outside of the housing via ports, or holes, located e.g., on one side of the housing, e.g., a top surface or cover of the housing. According to an embodiment, the housing can comprise a plurality of reagent pipetting positions located on an upper level in correspondence of respective pipetting holes for supplying reagent reconstitution liquid to the reagent containers and/or for withdrawing reconstituted reagents from the reagent containers. Thereby, access to the reagent containers can be provided without the need to take the reagent containers out of the housing.

The reagent management system can further comprise a reagent reconstitution device for reconstituting dry or lyophilized reagents or diluting concentrated liquid reagents of one or different types provided in reagent containers in order to carry out in-vitro diagnostic tests.

A "reagent reconstitution device" can be a group of functional units cooperating with each other or configured to carry out a series of consecutive or parallel steps aimed at reconstituting dry or lyophilized reagents or diluting concentrated liquid reagents. The term "reconstitution" can therefore be generally used to include both dissolving or re-suspending dry or lyophilized reagents into a determined amount of reconstitution liquid, and adding a determined amount of reconstitution (dilution) liquid to a concentrated liquid reagent, in order to obtain a final concentration of liquid reagent for use in a test. The reconstitution liquid can vary for different reagents; it can be, for example, water or a buffer composition or any other diluent or solvent, thereby making the reagents ready to use for testing.

A functional unit of the reagent reconstitution device can be a reagent container opening device. According to an embodiment, the reagent container opening device can be a piercer. The piercer may be configured as a rigid rod or needle-like device, having a sharpened tip and being movable at least in a direction of travel with respect to a closure of a reagent container in a reagent container opening position and through the pierceable closure in order to make a hole in the closure, thereby opening the reagent container. Alternatively, and/or in addition, a reagent container or reagent container holder may be moved with respect to the piercer such as the closure is pierced by the piercer.

Another functional unit of the reagent reconstitution device can be a reconstitution liquid dispenser adapted to transfer reconstitution liquid from a reconstitution liquid supply into an opened reagent container. The reconstitution liquid dispenser can be a pipetting device, comprising e.g., a needle, e.g., a steel needle, movable at least in one direction of travel with respect to the closure of a reagent container such as to pass through the hole formed through the closure by the piercer. Alternatively, the needle itself may have the function of a piercer. According to an embodiment, the reconstitution liquid dispenser can be a reagent pipetting device also adapted to withdraw reconstituted reagent from the same reagent container. According to an embodiment, the reconstitution liquid supply can be a system liquid supply and the reconstitution liquid is a system liquid. A "system liquid" can be a liquid medium, which can be used to minimize the amount of compressible medium such as air in the fluidic lines of the pipetting device and thereby increase the stiffness of the fluidic system and the precision of pipetting. The system liquid may be an aqueous liquid, e.g., water or other aqueous solution. A "reconstitution liquid supply" can either be a container containing the reconstitution liquid or a line conduit supply of reconstitution liquid, e.g., a pipeline water supply, where the water can possibly be deionized, degassed or otherwise treated to make it suitable as reagent reconstitution liquid. According to an embodiment the reagent reconstitution liquid supply can be a reagent reconstitution liquid container received in a receiving section of the reagent container section, e.g., a liquid container in a reagent container holder.

Another functional unit can be a reagent container agitating device or a liquid mixing device. A "reagent container agitating device" can be a device comprising at least one reagent container or reagent container holder receiving position that can be movable, e.g., shakable, vibratable, rotatable, such as to shake, vibrate, rotate a reagent container or a plurality of reagent containers in the same reagent container holder and thereby homogeneously reconstitute the reagent or reagents contained therein with the dispensed reagent reconstitution liquid. A "liquid mixing device" can be a mixer, e.g., a stirrer, paddle or the like that can be inserted in an open reagent container and mix the liquid contained therein for achieving substantially the same reconstitution result. However, any equivalent mixing technique or device suitable for agitating/mixing a liquid in the reagent container can be used, e.g. an ultrasound generator.

In one embodiment, the reagent container section may comprise a reagent container transport device to move reagent containers or reagent container holders between receiving positions, e.g., between any of a storing position, a reagent container opening position, a reconstitution liquid dispensing position and/or a reconstituted reagent pipetting position, an agitating or mixing position, an inlet/outlet receiving position. The reagent container transport device may be configured as a gripper or as a movable reagent receiving position, e.g., translatable in one, two or three dimensions, and comprising for example an engaging element, such as a push/pull element, gripper or the like for withdrawing a reagent container or reagent container holder from e.g., a receiving position and transferring the reagent container or reagent container holder to a different receiving position. The reagent container transport device may have additional features such as a reagent container information reader and/or writer, a reagent container or reagent container holder detecting sensor, e.g., an optical sensor.

According to an embodiment where the reagent container is a flow-through cartridge, the reconstitution liquid dispenser may be coupled to the inlet of the cartridge in order to make reconstitution liquid flow through the cartridge and reconstitute the dry or lyophilized reagent contained therein. The cartridge may comprise an internal fluidic structure that facilitates mixing. The reconstituted reagent may be collected via the outlet of the cartridge in a secondary reagent container, where it may be further mixed, e.g., by agitation, and from where it may be withdrawn, e.g., by pipetting, for testing.

The reagent management system can further comprise a controller programmed to instruct the reagent reconstitution device to automatically reconstitute a volume of a selected reagent type in one or more reagent containers, where the volume can be determined based at least on an open container stability time of the reconstituted reagent type for each reagent container and on a number of tests that can be carried out within the open container stability time of the reconstituted reagent type.

A "controller" can be a programmable logic controller running a computer-readable program provided with instructions to perform operations in accordance with an operation plan and in particular associated with reagent reconstitution.

The controller may have additional tasks other than those associated with reagent reconstitution. For example, the controller may manage other process operations involved in the carrying out of in-vitro diagnostic tests. Such operations may include but are not limited to withdrawing of reagents from the reagent container section and dispensing of reagents into reaction vessels, opening and/or closing of sample containers or piercing caps of sample containers, withdrawing of samples from sample containers and dispensing the samples into reaction vessels for reaction with the reagents, mixing samples with reagents, transporting of sample containers and/or reaction vessels, washing of pipetting nozzles and/or replacing of disposable tips, detecting the result of reactions or monitoring the progress of reactions. In one embodiment, the controller may comprise or cooperate with a scheduler, for executing a sequence of steps within a predefined cycle time for a number of cycle times, where the sequence of steps may comprise both reagent reconstitution steps and other steps involved in the carrying out of in-vitro diagnostic steps for an optimal sharing and use of functional resources. The controller may further determine the order of in-vitro diagnostic tests according to the assay type, urgency, and the like.

In particular, the operations can comprise keeping track of shelf lives, e.g., by scanning barcodes or reading other information carrying tags, e.g., when reagent containers or reagent container holder enter the reagent receiving section, and entering such information in a definition file or electronic register. The operations can also comprise keeping track of open container stability times for each reagent container that is opened, based on the time of opening and the open container stability time associated with each reagent type. In one embodiment, the controller may cooperate with a scheduler in order to take into account test orders and a number of scheduled process operations associated with the execution of the test orders in order to decide when and which reagent in which reagent container has to be reconstituted. By doing so in a logical manner, the controller can minimize reagent loss and maximize throughput by making reagents available when needed and optimizing the use of functional resources, especially those functional resources that may be shared for carrying out the tests and for reconstitution of the reagents needed for the tests, e.g., reagent pipetting units. In one embodiment, the controller may be programmed to schedule the reconstitution steps so that conflict with other scheduled operations to carry out the in-vitro diagnostic tests can be avoided. For example, reagent pipetting from an already reconstituted reagent container may be scheduled at a time when another reagent container is being opened or agitated or resting between agitation steps. Also, the controller may be programmed to set priorities for the use of functional resources, for example based on test priority, on the need to run calibration runs, control runs, and the like. When several reagents in a respective number of reagent containers have to be reconstituted as soon as possible, e.g., in view of a large number of tests, the controller may allow parallel reconstitution by scheduling the various reconstitution steps for different reagent containers in a manner that conflict between them when it comes to use of the same functional resources can be avoided, e.g., in a staggered manner. For example, when a reagent container is being opened, another can be provided with reagent reconstitution liquid, another can be agitated, another can be in a resting position and so on.

The controller can calculate a volume of a reagent type to be reconstituted. Such a "volume" can be a volume that can be fixed or variable up to a maximum volume of reconstituted reagent of that type that can be sufficient to carry out a predetermined number of tests before the reconstituted reagent expires. Since more than one reagent containers may be reconstituted in order to obtain the maximum volume, the term can refer to the sum of volumes of reconstituted reagents of the same type in one or more reagent containers. As there is a maximum volume, there can also be a minimum volume, which can be the volume of reconstituted reagent in one reagent container. This can mean that in case only one or a few in-vitro diagnostic tests can be ordered whereas the volume of reconstituted reagent in one reagent container can be sufficient for carrying out even more in-vitro diagnostic tests, it cannot be prevented that excess reagent is reconstituted. In order to reduce this risk, smaller reagent containers may be used, which then more often results in a plurality of reagent containers that have to be opened in order to reconstitute a sufficient volume of reagent. With respect to the term "available volume", this can refer to the volume of a reagent type that has already been reconstituted and for which the open container stability time has not yet expired. Since each reagent container may be opened individually and therefore the open container stability time can count from the time of opening, the open container stability time may not refer to a total available volume but to the individual opened reagent containers making up the total available volume. The available volume of a reagent type can thus change over time as the reagent is being used and as the open container stability time of reconstituted reagents in individual reagent containers eventually expires.

The controller can calculate a volume of a reconstituted reagent type that can be required for testing according to a received number or an expected number of test orders requiring that reagent type. This may require opening a plurality of reagent containers containing reagent of the same type. However, before doing so, the controller can also take into account how many tests can be carried out within the open container stability time for each reagent container that can be opened. The number of tests that can be carried out depends, of course, on the capacity of the reagent container but also for example on the sample processing throughput of the system, on the type of tests and therefore on the scheduled sequence of tests and the scheduled use of functional resources. If the volume of a reconstituted reagent type that is required for carrying out a predetermined number of tests is higher than the maximum allowed volume, the controller can allow reconstitution of only a lower volume of reagent up to a maximum volume that allows to carry out a maximum number of in-vitro diagnostic tests before the open container stability time expires. It can thus be prevented that reconstituted reagent expires before it can be used. The controller can monitor and/or calculate how the available volume changes with time and can decide when additional reagent containers have to be opened and additional volume of reagent of the same type has to be reconstituted. In general, the controller may be programmed to instruct the reagent reconstitution device to reconstitute additional reagent of the same type just before or at a convenient time, in terms of functional resource use, before the available volume of the reagent type becomes insufficient. In this way, it can be prevented that reagent containers are opened too much in advance of their intended use and the risk that reconstituted reagent expires before it is used is minimized and, at the same time, continuous availability of reconstituted reagent can be ensured. For this same reason, it may be preferable not to reconstitute a maximum volume at the beginning even if a large number of tests are already scheduled, since workflow changes, e.g., due to system errors, clogging of the pipetting devices, introduced extra-wash cycles and the like may cause testing delays and, therefore, can enhance the risk that reconstituted reagent expires before use.

The calculated volume of a reagent type to be finally reconstituted can be reagent type and/or test specific and can be calculated taking into account the probability or risk of wasting reconstituted reagent and the consequence of it. In one embodiment, the controller may apply one or more rules or combinations thereof in the calculation. For example, according to one rule, the shorter the open container stability time of a reagent type, the smaller the volume. According to another rule, the higher the relative cost of the reagent type, the smaller the volume. The term "relative cost" can refer to the manufacturing costs, material costs and product costs in general that typically relate to higher commercial prices in comparison to other reagent types. According to another rule, the lower the frequency of occurring test orders to be carried out with the reagent type, the smaller the volume. Here the "frequency of occurring test orders" may refer to a statistical frequency, e.g. average number of tests/day carried out with a particular reagent type, where the number is higher for routine tests and lower for rarer tests ordered in a minor number of cases. However, the frequency may depend also on user dependent factors. There might be, for example, days of the week and/or hours of the day with lower frequency than others, due to the fact, for example, that samples and/or orders can be collected only on some particular days of the week or hours of the day. The controller can be however reprogrammed to take into account long operation pauses, e.g., in view of personnel absence, e.g., vacation, laboratory closure times, or, on the contrary, in case of extraordinary demand (increased number of test orders). The volume of reagent to be reconstituted for any reagent type may be therefore set manually, where the controller may provide recommendation about the value to be set and/or to warn in case a calculated maximum volume is exceeded or prevent that a calculated maximum volume is exceeded.

The volume of a reagent type to be reconstituted can be calculated also taking into account the required number of quality control and/or calibration runs and/or the dead volume of a reagent container. From time to time, e.g., when a new reagent lot is reconstituted, or after a number of tests have been carried out, it may be required to run a new calibration or repeat a calibration. Similarly, it may be required, or recommended, to execute or repeat a control run with standard samples to check or guarantee the reliability of the tests. With respect to calibration a "lot calibration timeout" may be defined. This can define how long (in hours) a particular calibration record may be valid for a lot after it has been created. Also, a "lot calibration creation time limit" may be defined. This can define how long (in hours) a reagent can be used for a lot calibration after it has been opened. The controller can thus be responsible for keeping record of these additional time limits and to plan reconstitution also in view of the possibility to run a calibration within the allowed time limit.

The controller can thus be programmed to take into account also the volume of reconstituted reagents required for any other purpose that is not an in-vitro diagnostic test carried out on a patient sample. Also, depending on the shape and capacity of a reagent container and the pipetting method used to withdraw reconstituted reagent from the reagent container, it can be that some reconstituted reagent volume can remain unused in the reagent container and cannot therefore be counted for as available volume. This lost volume can be referred to as dead volume and may be excluded from the calculation.

The controller may thus calculate a different volume of any reagent type to be reconstituted at different times depending on any one or more of the above mentioned factors.

According to certain embodiments, the controller may delay additional reconstitution of the same reagent type until the available volume reaches or drops below a threshold value or is about to expire, i.e., a defined time before expiry of the open container stability time. When such a threshold value is reached or shortage of reconstituted reagent is imminent for any other reason, e.g., due to imminent expiration, incoming of new test orders, e.g., emergency tests, for which the available volume would be insufficient, automatic reconstitution of additional reagent can be triggered.

The threshold value can be user configurable and/or can be determined by the controller according to the reagent type and/or test type. In one embodiment, it can be set according to any one or more rules or combinations thereof analogously to the calculation of the volume to be reconstituted.

According to one rule, the shorter the open container stability time of the reagent type, the lower the threshold value. According to another rule, the higher the relative cost of the reagent type, the lower the threshold value. According to another rule the lower the frequency of occurring test orders to be carried out with the reagent type, the lower the threshold value.

The automatic trigger of automatic reconstitution can be overruled according to certain embodiments. In one embodiment, the user may prevent automatic reconstitution of additional reagent(s), e.g., by resetting the threshold value (no threshold value). Also, the controller may be programmed to ask for user confirmation or to check verification of other conditions and/or is reprogrammable in order to take into account user specific time change requests before instructing the reagent reconstitution device to reconstitute additional reagent(s). In this manner, it can be prevented that reagents continue being reconstituted even if not needed, e.g., in view of reduced test frequency occurring in some days of the week and/or hours of the day, night breaks, long operation pauses, e.g. in view of personnel absence, e.g., vacation, laboratory closure times. Therefore, it can be prevented that reagents are reconstituted that would expire before even being used.

Analogously, the controller can be programmed to instruct the reconstitution device to start reconstitution of a reagent type at a pre-defined time preceding an expected number of test orders, e.g., just before the beginning of a personnel shift or operational day, or at recurring intervals or within a user configurable timespan, e.g., equating the time of a personnel shift, or after an initial number of test orders to be carried out with that reagent type is reached.

The controller can be programmed to keep record of reagent shelf lives in reagent containers or lots of reagent containers in the reagent container section and, according to certain embodiments, for each reagent type to instruct the reconstitution device to reconstitute first reagents in those reagent containers or lots with the shortest remaining shelf life and/or reagents whose open container stability time would otherwise become shorter because close to the end of the shelf life. The controller, thus, can control that reagents expiring first (closer expiry date) are first reconstituted and can prevent that reagents remain unused before the end of their shelf life. Also, if reagent containers of different capacity are available, the controller may be programmed to instruct the reconstitution device to reconstitute first reagents in those reagent containers with the smallest capacity. By doing so, the chance that already reconstituted reagent is used up before additional reagent is reconstituted can be increased.

Should the shelf life of a reagent or open stability time of a reconstituted reagent nevertheless expire, that reagent in that particular reagent container can be locked by the controller for further use. Also, the controller may be programmed to automatically dismiss, e.g., unload or move to an outlet receiving position, reagent containers or reagent container holders comprising expired reagents.

Also, the controller may be programmed to prioritize reagent reconstitution according to reagent type and/or test type. For example, priority can be given to the reconstitution of those reagent types in those reagent containers or lots that can be needed to carry out emergency tests or to those that can be needed for calibration or control runs, or those that can be purposely inserted in a dedicated priority receiving position of the reagent container section.

According to certain embodiments, the reagent management system can further comprise a user interface. A "user interface" can be a software providing tools to interact with the controller, e.g., by exchanging information or orders with the controller. Interaction may conveniently occur via a visual display. The display may be a touch display or be connected to a keyboard, mouse, touch pad or the like. In one embodiment, via the user interface, it can be possible to program the controller in order to set or change rules, schedules, plans and priorities, values, thresholds, in relation to the automatic reconstitution of reagents. Via the user interface, it can also be possible to display settings and to monitor reagent statuses, such as for example remaining shelf lives for individual reagent containers, reagent container holders or lots, remaining open stability times for individual reagent containers, available volume of each reagent type, scheduled reconstitution plans and reconstitution steps, number and type of tests for which currently available volumes of any reagent type is sufficient for, schedule of run and control tests, and the like. Conveniently, only a "use until" date or time may be displayed, that can be the earliest to expire between the shelf-life and the open container stability time. The user interface may also provide information with respect to reagent container identity and position in the reagent container section, its relative status such as closed, open, reconstituted or in reconstitution process. According to an embodiment, the user may select via the user interface the particular reagent containers for reconstitution. However, the user may only select which reagent type should be reconstituted, or only which tests have to be carried out and the controller selects the reagent container(s) or reagent container holder(s) containing that reagent type to be reconstituted. Also, the user interface may prompt the user to remove used or expired reagent containers from the reagent container sections and/or to provide additional reagent containers to the reagent container section.

A method of automatically reconstituting a dry, or lyophilized, reagent or a concentrated liquid reagent provided in a reagent container in order to carry out an in-vitro diagnostic test with the reconstituted reagent is also disclosed. The method can comprise opening the reagent container and dispensing a volume of reconstitution liquid into the reagent container. The method can further comprise agitating the reagent container for reconstituting the reagent in the reconstitution liquid. The method can further comprise maintaining the reagent container at rest for a predefined time. The method may further comprise repeating agitation of the reagent container for at least a second time.

According to an embodiment, the method can further comprise transporting the reagent container to a reagent container opening position for opening the reagent container, from the reagent container opening position to a reconstitution liquid dispensing position for dispensing the reconstitution liquid, from the reconstitution liquid dispensing position to an agitating position for agitating the reagent container, from the agitating position to a storing position for resting, optionally from the storing position to the agitating position for agitating the reagent container a second time.

According to an embodiment, opening the reagent container can comprise piercing a pierceable closure of the reagent container and dispensing the reconstitution liquid can comprise dispensing through the pierced closure.

According to an embodiment, the reagent can be a coagulation reagent or a hematology reagent and the in-vitro diagnostic test can be a coagulation test or a hematology test respectively.

According to certain embodiments, the method can comprise parallel reconstituting a plurality of reagent containers, the parallel reconstitution comprising scheduling the different reconstitution steps in a staggered manner for different reagent containers so that conflict between functional resources can be avoided.

According to certain embodiments, the method can further comprise performing a reagent volume check. A "reagent volume check" can be an operation following reagent reconstitution aimed at determining whether the reconstituted volume in a reagent container corresponds to the specified volume or lies in a tolerance range about the specified volume. A possible reason why this may not be the case, despite dispensing of the correct amount of reconstitution liquid, is that the reagent container may be damaged and therefore leaking. The risk that such a case can occur is higher for example for glass reagents containers that can be broken during handling, e.g., due to dropping or impact, and may not be directly detectable if, for example, the reagent container is closed and hidden in a reagent container holder. A reagent volume check may therefore be useful to indirectly verify integrity and therefore shelf life of a reagent container before use. According to an embodiment, the reagent volume check can comprise inserting a reagent pipetting device into a reagent container to a position where the surface level of the reconstituted reagent is expected to be, aspirating a predefined volume of fluid, dispensing the aspirated volume of fluid into a secondary vessel and performing liquid level detection of the dispensed fluid in the secondary vessel, confirming or determining the reagent volume in the reagent container if liquid level is detected in the secondary vessel. According to an embodiment, detection of liquid level can be a capacitive and/or resistive liquid level detection resulting in a change of electrical capacitance or resistance when a probe, e.g., a metal needle, e.g., a pipetting needle, contacts the liquid surface. Other liquid level detection methods and tools known in the art can be however used, e.g. optical methods, ultrasonic methods and the like.

According to an embodiment, the method can comprise pooling of the reconstituted reagent in at least one reagent container into a second reagent container and performing a calibration run from the pooled reagent container. Pooling may have the advantage of saving reagent for calibration as calibration is carried out only once for the entire pool, however at the cost of increased reagent preparation time and increased use of functional resources for transferring reagents between reagent containers.

A further method of automatically reconstituting dry or lyophilized reagents or concentrated liquid reagents provided in reagent containers in order to carry out in-vitro diagnostic tests with the reconstituted reagents is also disclosed.

The method can comprise receiving information about a number of in-vitro diagnostics tests to be carried out. For example, the user can select the type and number of tests to be carried out based on received orders or expected orders, e.g. manually or by scanning barcodes or reading any other sample-specific information-carrying tag. Also for example, the reagent management system can automatically register orders when samples enter the system, e.g. by reading barcodes or any other sample-specific information-carrying tag. Also for example, the controller can be connected to a laboratory information system (LIS) or hospital information system (HIS) in order to automatically track incoming orders and prepare for the incoming orders. In this context, the controller may also be connected to an inventory management system, e.g. for ordering new reagent containers and replace used or expired reagent containers in the reagent container section.

The method can further comprise automatically calculating a total volume of reconstituted reagent for any reagent type that may be required to carry out the in-vitro diagnostic tests.

The method can further comprise determining if a volume of reconstituted reagent of the same reagent type is already available and determining its open container stability time (remaining open container stability time).

The method can further comprise determining a number of in-vitro diagnostic tests that can be carried out within the open container stability time of the already available reconstituted reagent, and if the number is lower than the number of in-vitro diagnostic tests that have to be carried out, calculating an additional volume of reagent of the same type that is required, and if the open container stability time of the reagent containers to be opened to obtain the required additional volume would be insufficient to carry out the in-vitro diagnostic tests, opening only a limited number of containers and reconstituting only a volume of reagent that can be used within the open container stability time.

According to an embodiment, the method can comprise automatically overruling a manually set volume of reagent to be reconstituted, or providing recommendation about a value to be set, and/or providing a warning, in case a calculated maximum volume is exceeded, or preventing that a calculated maximum volume is exceeded when manually setting the volume.

According to an embodiment, the method can comprise monitoring the available volume of reconstituted reagent and/or calculating how the available volume changes over time for each reagent type and scheduling reconstitution of an additional volume at a convenient time ahead of scheduled or expected in-vitro diagnostic tests, as long as the reconstituted reagent, including the already available reagent and the additional reconstituted reagent can be used within the open container stability time, or when the available volume reaches or drops below a threshold value or when the open container stability time is about to expire.

In calculating the volume of reagent to be reconstituted at any given time, the same logics described above with respect to other embodiments may also apply.

Referring initially to FIG. 1, FIG. 1 shows an example of system 100 for in-vitro diagnostics, and, in particular, a coagulation analyzer. FIGS. 2-5 show parts of the system 100 of FIG. 1 in more detail and are to be viewed together for better understanding. The system 100 can comprise a reagent management system 110 comprising a reagent container section 112 integrated as a module in the system 100 for receiving reagent containers and for reconstituting dry, or lyophilized, reagents provided in the reagent containers in order to carry out in-vitro diagnostic tests with the reconstituted reagents. The system 100 can further comprise a sample loading/unloading unit 190 for loading/unloading sample tube racks 191 comprising sample tubes. The system can further comprise a central vessel processing area 130. The vessel processing area 130 can comprise a vessel holder 140, the vessel holder 140 comprising a plurality of vessel holding positions 141. The vessel processing area 130 can further comprise a vessel input station 150 for feeding a vessel at a time to the vessel holder 140. The vessel processing area 130 can further comprise a movable vessel workstation 160 linearly translatable with respect to the vessel holder 140 and functionally coupled to the vessel holder 140 to transfer vessels between vessel holding positions 141 of the vessel holder 140. In one embodiment, at least some of the vessel holding positions 141 can be detection positions adapted to the measurement, e.g. optical measurement, of the result of the reaction between test liquids and reagents in vessels.

Figure 2:
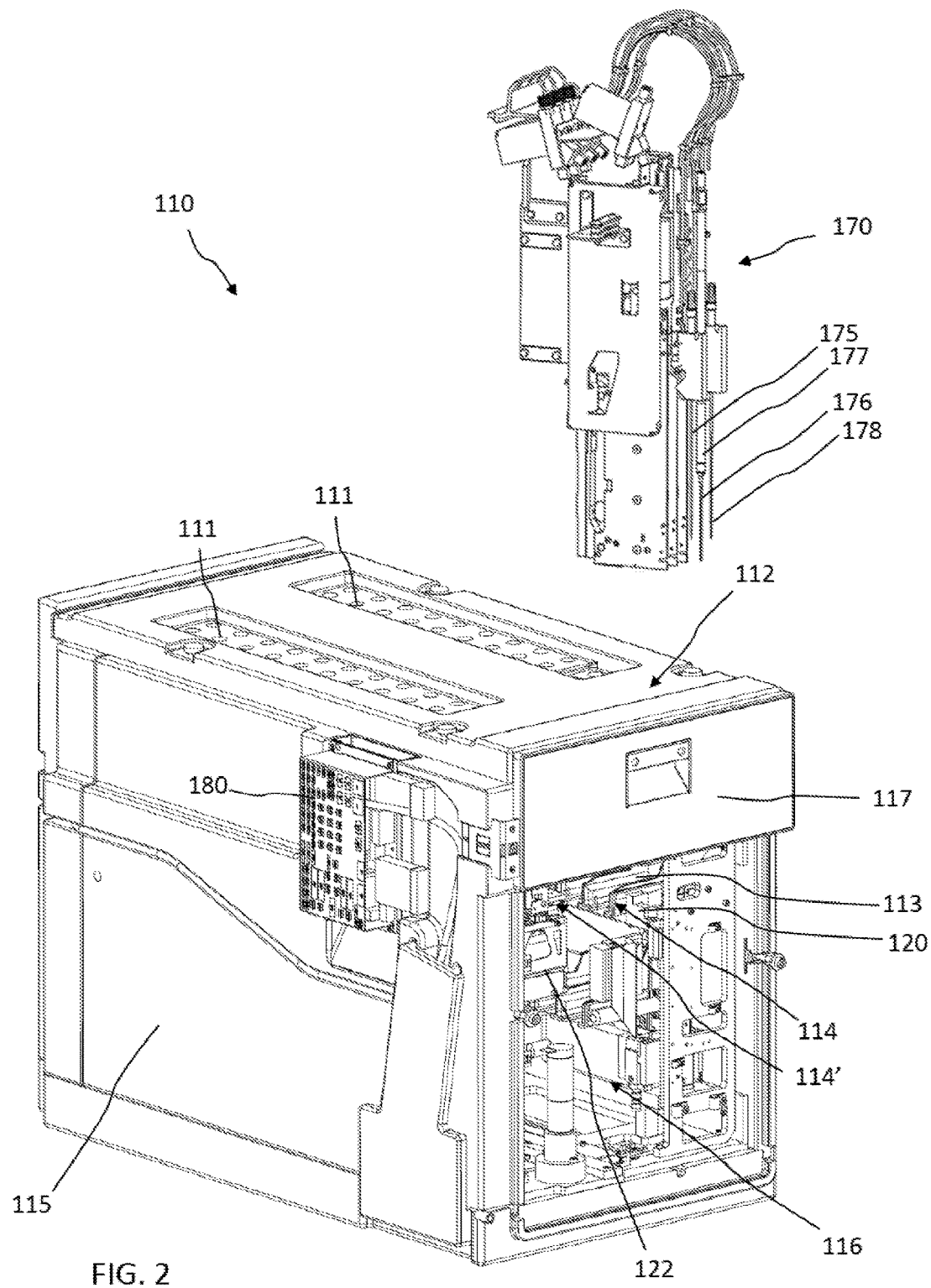
FIG. 2 illustrates parts of a reagent management system according to an embodiment of the present disclosure.

The system 100 can further comprise a pipette head 170 comprising three pipetting devices (shown in FIG. 2). In one embodiment, the pipette head 170 can be translatably mounted on a horizontal arm 171 and the arm 171 can be translatably coupled to an orthogonal guide rail 172. The pipette head 170 can thus be movable in a space above the reagent management system 110, above the vessel processing area 130, and above the sample loading/unloading unit 190. In addition, the pipetting devices can each be individually translatable in a vertical direction such as to be able to access a reagent container in the reagent management system 110 via holes 111, a sample tube in the sample loading/unloading unit 190 and a vessel in the vessel processing area 130. In one embodiment, with the same pipette head 170, test liquids can be aspirated from sample tubes in the sample loading/unloading unit 190, reagents can be aspirated from reagent containers in the reagent management system 110 and both test liquids and reagents can be dispensed into vessels in the vessel processing area 130. The pipetting head 170 and respective pipetting devices can therefore be a shared functional resource between the reagent management system 110, the sample loading/unloading unit 190 and the vessel processing area 130.

Figure 3:
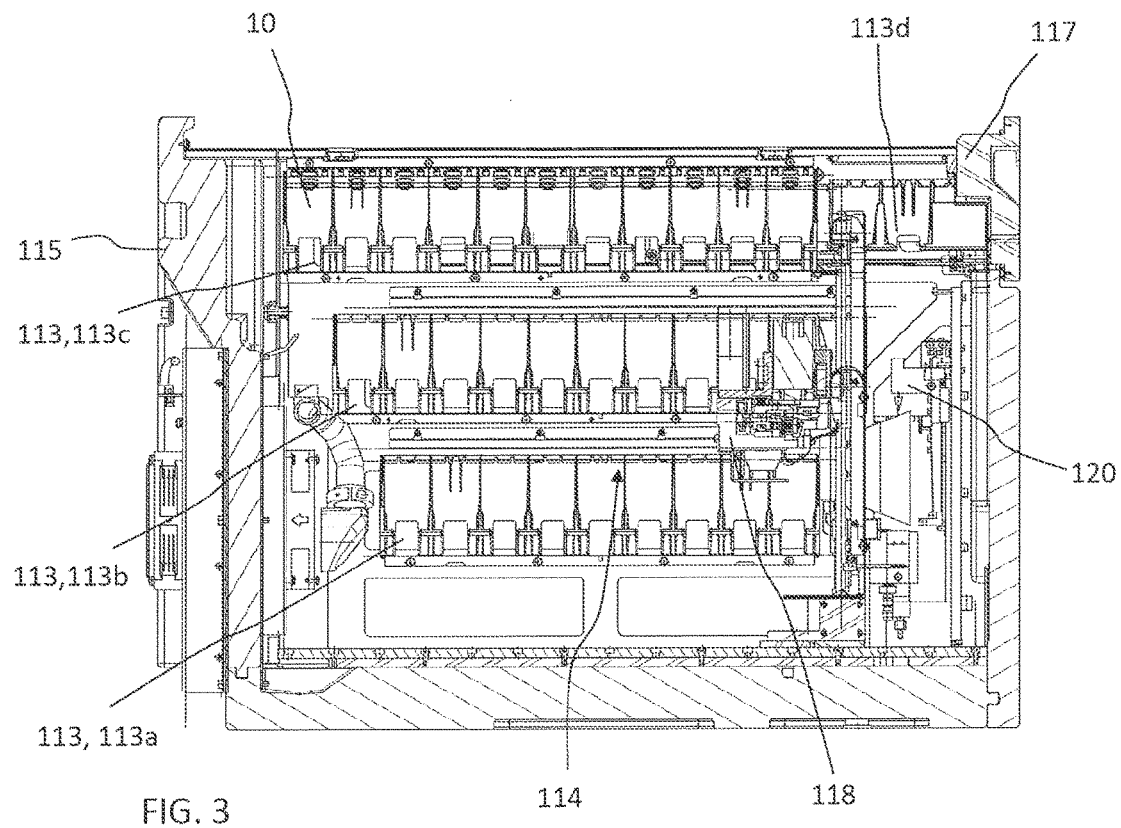
FIG. 3 illustrates a cross-sectional view of a reagent container section according to an embodiment of the present disclosure.

FIG. 2 shows parts of the reagent management system 110 in more detail including the reagent container section 112 (front removed for clarity) and the pipette head 170. FIG. 3 shows the reagent container section 112 in cross section.

The pipette head 170 can have a sample/reagent pipette head comprising a first reagent pipetting device 175, a second reagent pipetting device 176 and a sample pipetting device 178. The second reagent pipetting device 176 can comprise a heating element 177 for heating a reagent to an optimal temperature between reagent aspiration and reagent dispensing. The sample pipetting device 178 can be adapted to pipette test liquids from sample tubes, e.g. including aspiration through a closure of a sample tube by piercing the closure. The reagent container section 112 can be adapted for receiving reagent containers in reagent container holders 10 and can comprise access holes 111 on the top surface for the pipetting nozzles 175, 176 to enter the reagent container section 112 and to access the reagent containers contained therein, e.g. in order to withdraw an aliquot of reconstituted reagent from a reagent container or to add reconstitution liquid to a dry or lyophilized reagent in a reagent container.

Figure 4:
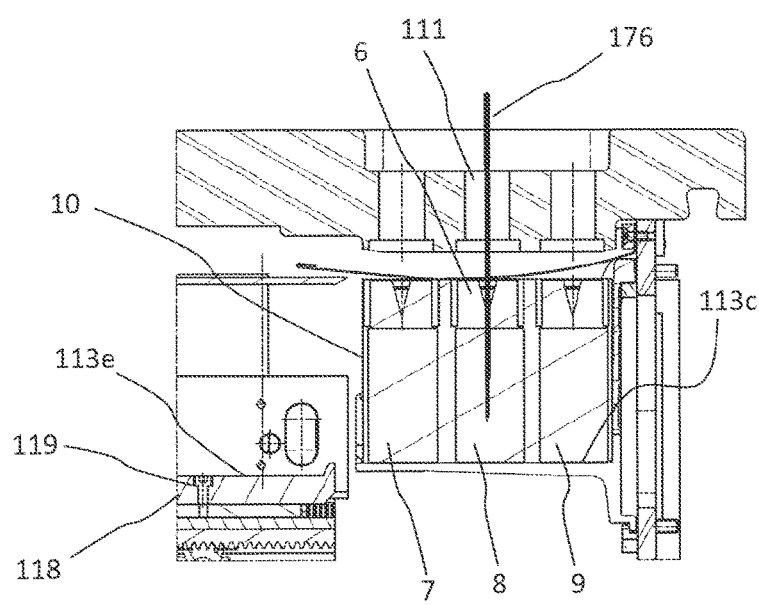
FIG. 4 illustrates a detail of the reagent container section of FIG. 3 according to an embodiment of the present disclosure.

In one embodiment, the reagent container section 112 can be embodied as a closed and refrigerated compartment comprising a housing 115 and an inner space 116 comprising a plurality of slots 113 acting as receiving positions for accommodating reagent container holders 10. The receiving positions 113 can be arranged in two multi-level blocks 114, 114', on two sides of the inner space 116 respectively facing each other. Each block 114, 114' can comprise three levels, each level comprising a plurality of receiving positions 113 arranged linearly next to each other, thereby forming a compact yet high-capacity three-dimensional arrangement. The receiving positions 113 can have different functions. In this case, the receiving positions 113a, 113b on the lower and middle level of each block 114, 114' can act as storing/resting positions for reagent container holders 10 whereas the receiving positions 113c on the third and uppermost level can be reconstitution liquid dispensing positions and/or pipetting positions for withdrawing reconstituted reagents from the reagent containers in the reagent container holders 10 via the reagent pipetting devices 175, 176 through holes 111. Thus only the reagent containers 10 in the receiving positions 113c of the upper level can be accessible by the pipetting devices 175, 176 and can act therefore as pipetting positions. FIG. 4 provides a more detailed cross-sectional view of a reagent container holder 10 comprising 3 reagent containers 7, 8, 9 in one of the upper receiving positions 113c and one of the reagent containers 8 being accessed by one of the reagent pipetting devices 176 via an access hole 111 in the cover of the housing 115. In one embodiment, the pipetting device 176 can be inserted into the reagent container 8 via a pierced cap 6 in order e.g. to withdraw an aliquot of reconstituted reagent contained therein or to add reconstitution liquid to a dry, or lyophilized, reagent or concentrated liquid reagent contained therein.

The reagent container section 112 can further comprise an inlet/outlet drawer-like interface 117 comprising inlet/outlet receiving positions 113d for introducing and removing reagent container holders 10 into/from the reagent container section 112.

The reagent container section 112 can further comprise a reagent container transport device 118 to move reagent containers between different reagent container holder receiving positions 113. In one embodiment, the reagent container transport device 118 can be arranged in the inner space 116 and can be linearly translatable longitudinally between the two blocks 114, 114' in a horizontal direction. In addition, the reagent container transport device 118 can comprise a reagent container holder transfer position 113e translatable in the vertical direction that can be entered from two opposite sides facing the blocks 114, 114' respectively. The reagent container holder transfer position 113e can therefore be brought in alignment with any of the receiving positions 113a, 113b, 113c on any level of the two blocks 114, 114' respectively as e.g., shown in FIG. 4. The reagent container transport device 118 can further comprise an engaging element 119, that can be translatable with respect to the reagent container holder transport position 113e such as to engage with the bottom of a reagent container holder 10 and withdraw a reagent container holder 10 from e.g., a receiving position 113 or push a reagent container holder 10 into a receiving position 113. Thus a reagent container holders 10 can be easily moved between different receiving positions 113, e.g., between a storing receiving position 113a, 113b and a reagent pipetting position 113c or vice versa. Moreover the reagent container holder transfer position 113e can be brought in alignment also with any of the inlet/outlet receiving positions 113d in order to transfer new reagent container holders 10 into e.g., any storing receiving position 113a, 113b or to transfer any used or expired reagent container holder 10 from e.g., a storing receiving position 113a, 113b to an outlet receiving position 113d.

The disclosed reagent management system 110 can further comprise a reagent reconstitution device for reconstituting reagents of one or different types provided in the reagent containers 7, 8, 9 in order to carry out in-vitro diagnostic tests with the reconstituted reagents. The reagent reconstitution device can comprise multiple functional units.

Figure 5:
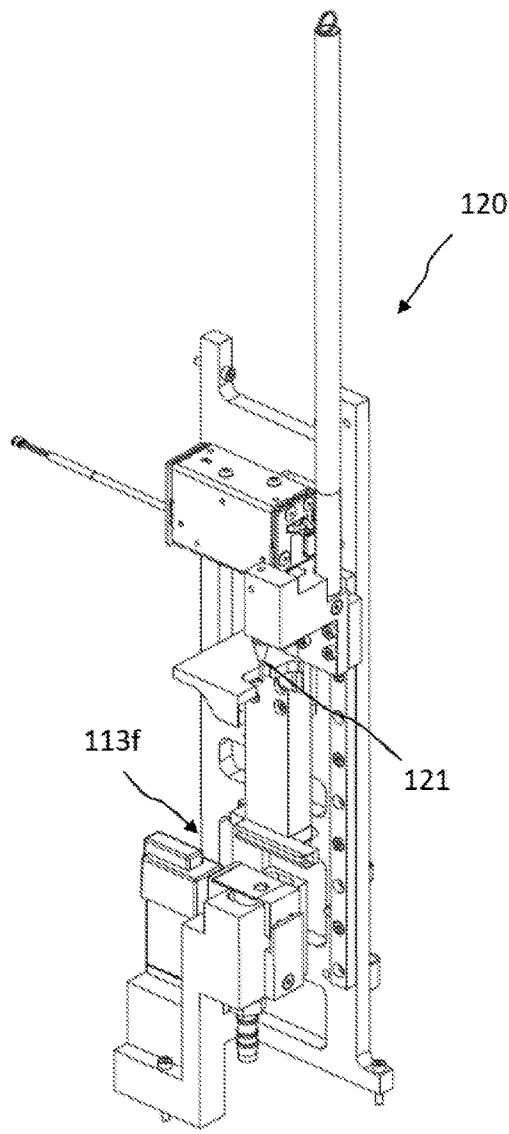
FIG. 5 illustrates a reagent container opening device according to an embodiment of the present disclosure.

In one embodiment, the reagent reconstitution device can comprise a piercer 120, illustrated in more detail in FIG. 5. The piercer 120 can comprise a reagent container opening position 113f, in this case a reagent container piercing position 113f, for receiving a reagent container holder 10 comprising reagent containers 7, 8, 9, the reagent containers 7,8,9 comprising pierceable closures 6 to be pierced. The reagent container transport device 118 and, in one embodiment, the reagent container holder transport position 113e can be brought in alignment also with the piercing position 113f for transferring reagent container holders 10 to and from the piercing position 113f. The piercer 120 can further comprise a spike 121 having a sharpened tip that can be translatable towards and away from a closure 6 of a reagent container 7, 8, 9 in a reagent container holder 10 when this is received in the reagent container piercing position 113f in order to make a hole in the closure 6, thereby opening the reagent container 7, 8, 9. Whereas only one spike 121 is shown for sequential opening of different reagent containers 7, 8, 9 several spikes 121 or equivalent piercers may be provided for parallel opening. Also, the spike(s) 121 may be fixed whereas the reagent container piercing position 113f may be made translatable.

Another functional unit of the reagent reconstitution device can be the pipetting head 170 and, in particular, the reagent pipetting devices 175, 176 that can act also as reconstitution liquid dispensers to transfer reconstitution liquid into opened reagent containers 7, 8, 9. The reconstitution liquid can, in this case, be a system liquid such as, water.

Figure 6:
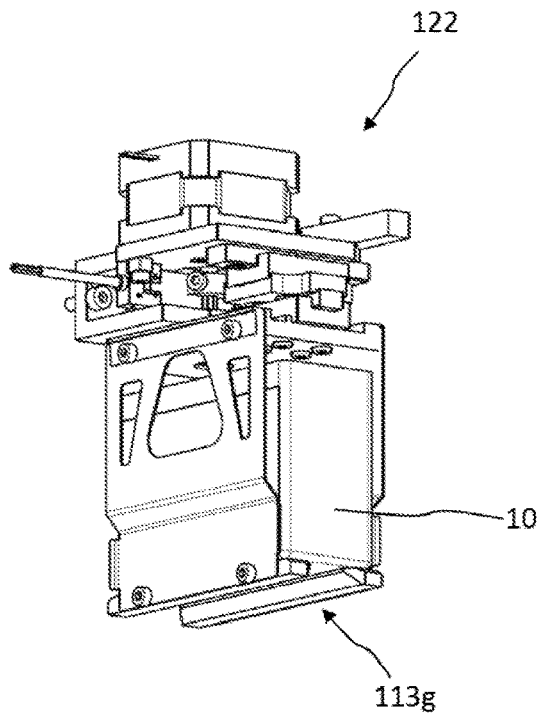
FIG. 6 illustrates a reagent container agitating device according to an embodiment of the present disclosure.

Another functional unit can be a reagent container agitating device 122, illustrated in more detail in FIG. 6. The reagent container agitating device 122 can comprise a reagent container holder agitating position 113g that can be shakable such as to shake a plurality of reagent containers 7, 8, 9 in the same reagent container holder 10 and thereby homogeneously reconstitute the reagent or reagents contained therein with the dispensed reagent reconstitution liquid. Analogously to the other receiving positions 113a, 113b, 113c, 113d, 113f, the reagent container transport position 113e can be brought into alignment also with the reagent container holder agitating position 113g for transferring a reagent container holder 10 into or from the reagent container holder agitating position 113g.

The reagent container transport device 118 can therefore itself also be a functional unit of the reagent reconstitution device, although it can be used independently to move reagent container holders 10 between different receiving positions 113a, 113b, 113c of the blocks 114, 114' according to the needs, e.g. to bring a requested reagent container holder 10 for carrying out a diagnostic test to the upper level for pipetting when needed and return it to a lower level when not needed.

In this case, the reagent container holder 10 can be configured as a reagent pack or cassette comprising three reagent containers 7, 8, 9, at least some of the reagent containers 7, 8, 9 of at least some reagent containers holders 10 containing a dry or lyophilized reagent or a concentrated liquid reagent for carrying out in-vitro diagnostic tests when reconstituted, where the reagent may be the same in each reagent container 7, 8, 9 of the same reagent container holder 10 or may be different. Also the size of the reagent containers 7, 8, 9 may vary between them or between different reagent container holders 10, whereas the reagent container holder 10 can remain of the same size that fits any of a reagent container holder storing position 113a, 113b, a reagent container holder piercing position 113f, a reconstitution liquid dispensing position and/or a reconstituted reagent pipetting position 113c, a reagent container holder agitating position 113g, a reagent container holder transport position 113e, a reagent container holder inlet/outlet receiving position 113d. In this case, the dry or lyophilized reagent can be a coagulation reagent and the concentrated liquid reagent can be a hematology reagent respectively.

Figure 7:
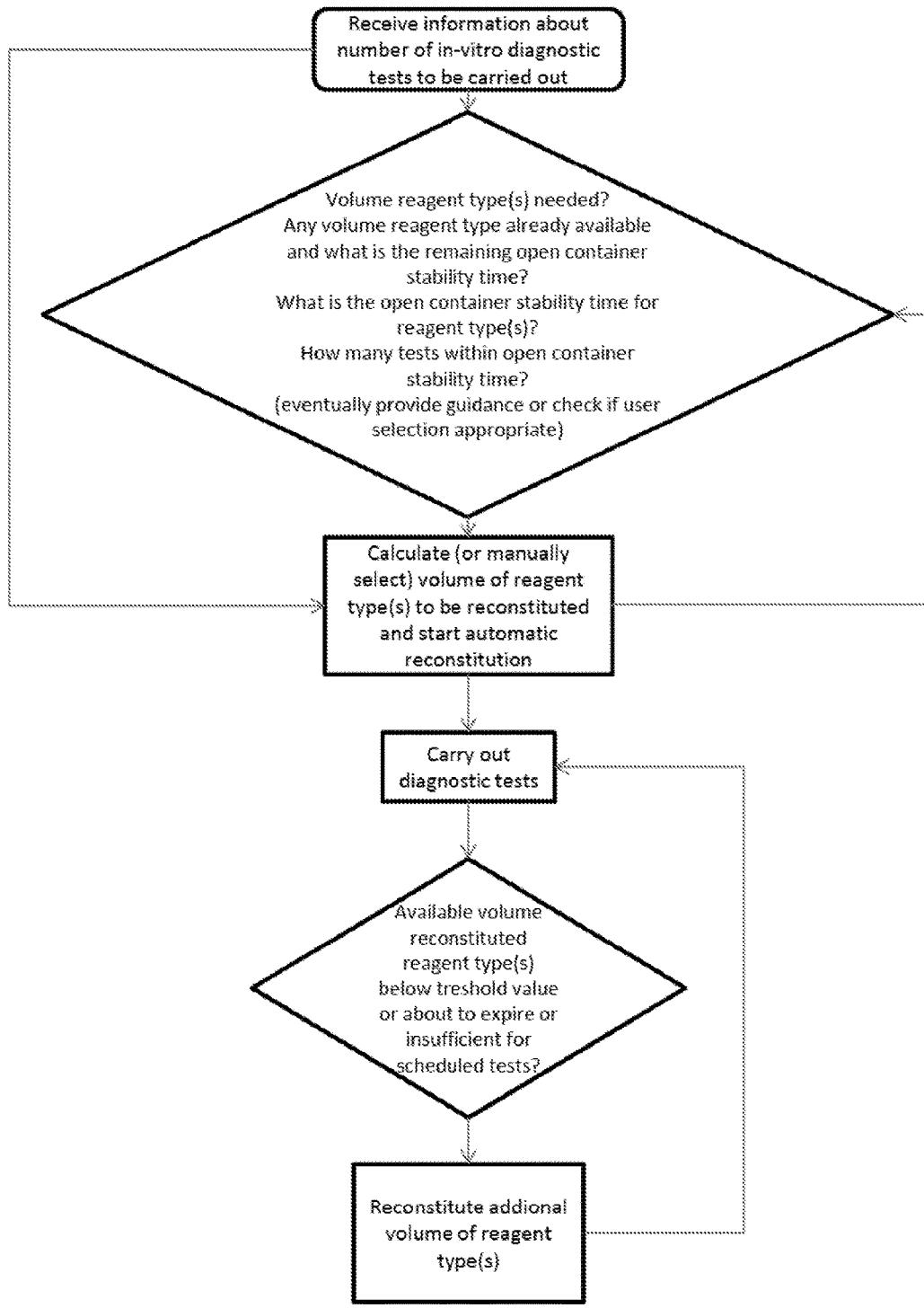
FIG. 7 illustrates a flow diagram illustrating generally a controller run program according to an embodiment of the present disclosure.

The system 100 can further comprise a controller 180 programmed to control the execution of a number of scheduled process operations including instructing the reagent reconstitution device to automatically reconstitute a volume of a selected reagent type in one or more reagent containers 7, 8, 9 in one or more reagent container holders 10, where the controller (180) can calculate the volume based at least on an open container stability time of the reconstituted reagent type for each reagent container 7, 8, 9 and on a number of tests that can be carried out within the open container stability time of the reconstituted reagent type. The process operation plan can include other operations as in part schematically illustrated in FIG. 7. In general, the controller 180 can start receiving information about a number of in-vitro diagnostics tests to be carried out. This information may be entered for example by a user, who can select via a user interface (not shown) the type and number of tests to be carried out based on received orders or expected orders. The controller 180 may be however connected to a laboratory information system (LIS) or hospital information system (HIS) (not shown) in order to automatically track incoming orders and prepare for incoming orders. Orders may be also automatically registered by the controller 180 as test liquids enter the sample loading/unloading unit 190. The controller 180 can then automatically calculate a total volume of reconstituted reagent for any reagent type that may be required to carry out the in-vitro diagnostic tests.

The controller 180 can then determine if reconstituted reagent that has not yet expired can still be available in the reagent container section 112 as well as its remaining open container stability time. If a volume of reconstituted reagent of the same reagent type is already available, the controller 180 can determine the number of in-vitro diagnostic tests that can be carried out within the remaining open container stability time, and if the number is lower than the number of in-vitro diagnostic tests that have to be carried out, it can calculate an additional volume of reagent of the same type that may be required. However, if the open container stability time of the reagent containers to be opened in order to obtain the required additional volume would be insufficient to carry out the in-vitro diagnostic tests, the controller 180 can instruct the reagent reconstitution device to open only a limited number of containers and reconstitute only a volume of reagent that can be used within the open container stability time.

Thus, the additional volume can be adapted accordingly for each reagent type. Alternatively, a user can set manually the initial total volume, i.e., order reconstitution of a desired volume of reagent type whereas the controller 180 can provide guidance or check the user request by e.g. providing recommendations about the value to be set and/or warning in case a calculated maximum volume is exceeded or preventing that a calculated maximum volume is exceeded.

The controller 180 can also be programmed to monitor the available volume of reconstituted reagent and/or to calculate how the available volume changes over time for each reagent type and to schedule reconstitution of an additional volume at a convenient time ahead of scheduled or expected in-vitro diagnostic tests, as long as the reconstituted reagent, including the already available reagent and the additional reconstituted reagent can be used within the open container stability time, or when the available volume reaches or drops below a threshold value or when the open container stability time is about to expire. The threshold value can be user configurable and/or can be set by the controller 180 according to the reagent type or test. Also, the controller 180 can be programmed to ask for user confirmation and can be reprogrammable in order to take into account user specific time change requests before instructing the reagent reconstitution device to reconstitute additional reagent(s). Typically, reconstitution of additional reagent(s) can continue as long as test orders are pending or expected or until the user does not reset the threshold value.

The controller 180 can be programmed via user interface to start automatic reconstitution at any time, e.g., soon or at a later time, e.g., at a pre-defined time preceding an expected number of test orders or within a user configurable timespan or after an initial number of test orders to be carried out with that reagent type is reached, so that reconstituted reagents can be ready and available to be used and the system 100 can start at once to execute the in-vitro diagnostic tests without having to wait for the reagents to be reconstituted.

Figure 8:
FIG. 8 illustrates schematically a method of automatically reconstituting reagents according to an embodiment of the present disclosure.

FIG. 8 schematically depicts a method of automatically reconstituting reagents. In one embodiment, the method can be directed to automatic reconstitution of a dry, or lyophilized, or a concentrated liquid reagent provided in a reagent container 7, 8, 9 in order to carry out an in-vitro diagnostic test with the reconstituted reagent. The method can comprise piercing (P) a pierceable closure 6 of the reagent container 7, 8, 9, e.g. using the piercer 120 of FIG. 5. The method can further comprise dispensing (D) a volume of reconstitution liquid into the reagent container through the pierced closure, e.g. via a reagent pipetting device 175, 176. The method can further comprise agitating (A) the reagent container 7, 8, 9, in this case by agitating the reagent container holder 10, for reconstituting the dry, or lyophilized, or concentrated, reagent in the reconstitution liquid, e.g., by the reagent container agitating device 122 of FIG. 6. The method can further comprise maintaining the reagent container 7, 8, 9 at rest (R) for a predefined time, e.g., about 30 min. The method can optionally comprise agitating (A) the reagent container 7, 8, 9 for at least a second time.

The method can comprise transporting the reagent container 7, 8, 9, by transporting the reagent container holder 10, within the reagent container section 112 from a storing position 113a, 113b to the reagent container holder piercing position 113f for piercing, from the reagent container holder piercing position 113f to a reconstitution liquid dispensing position 113c for dispensing the reconstitution liquid, from the reconstitution liquid dispensing position 113c to the reagent container holder agitating position 113g for agitating the reagent container holder 10, from the reagent container holder agitating position 113g to a reagent container holder storing position 113a, 113b for resting, optionally from the reagent container holder storing position 113a, 113b to the reagent container holder agitating position 113g for agitating the reagent container holder 10 a second time.

The method can optionally further comprise performing a reagent volume check (C). The reagent volume check (C) can comprise (not shown) inserting a reagent pipetting device 175, 176 through the pierced closure 6 to a position where the surface level of the reconstituted reagent is expected to be, aspirating a predefined volume of fluid, dispensing the aspirated volume of fluid into a secondary vessel (outside of the reagent container section 112), performing liquid level detection of the dispensed fluid in the secondary vessel, confirming or determining the reagent volume in the reagent container 7,8,9 if liquid level is detected in the secondary vessel.

Figure 9:
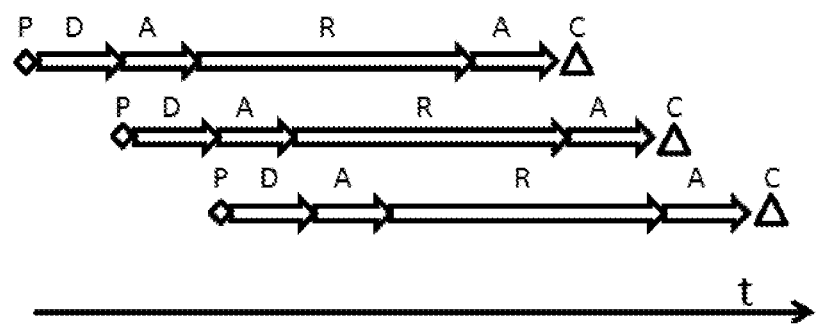
FIG. 9 illustrates schematically a variant of the method of FIG. 8 for parallel reconstitution according to an embodiment of the present disclosure.

FIG. 9 schematically depicts a variant of the method of FIG. 8 for parallel reconstitution. In one embodiment, the method can comprise parallel reconstituting a plurality of reagent containers 7, 8, 9 containing the same or different reagent types according to the need in different reagent container holders 10 or outside of reagent container holders 10, the parallel reconstitution comprising scheduling the different reconstitution steps in a staggered manner for different reagent containers so that conflict between functional resources can be avoided (t represents a time line in the figure). This can mean for example that whereas piercing (P) can be performed on one reagent container, 7, 8, 9 dispensing (D) of reconstitution liquid can be performed on another reagent container 7, 8, 9 (that was previously pierced), agitating (A) can be performed on yet another reagent container 7, 8, 9, to which reconstitution liquid was previously added and so on. If a diagnostic test is being performed during reagent reconstitution, the controller 180 can ensure that withdrawing an aliquot of reagent from an already reconstituted reagent container 7, 8, 9 can be scheduled at a time when the pipetting device 175, 176 is not used for dispensing reconstitution liquid or making a volume check with respect to another reagent container being reconstituted. In other words, pipetting of reconstituted reagent for diagnostic testing and reconstitution steps involving the use of the same pipetting devices 175, 176 as shared functional resource can be scheduled at different times respectively.

Figure 10:
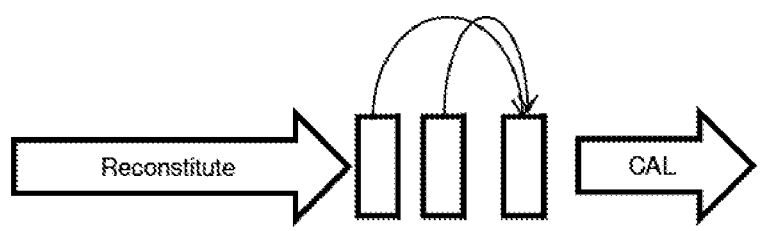
FIG. 10 illustrates schematically an option of pooling reconstituted reagents according to an embodiment of the present disclosure.

According to an embodiment, as schematically depicted in FIG. 10, the method can comprise pooling of the reconstituted reagent (of the same type) in at least one reagent container into a second reagent container and performing a calibration run (CAL) from the pooled reagent container.

Figure 11:
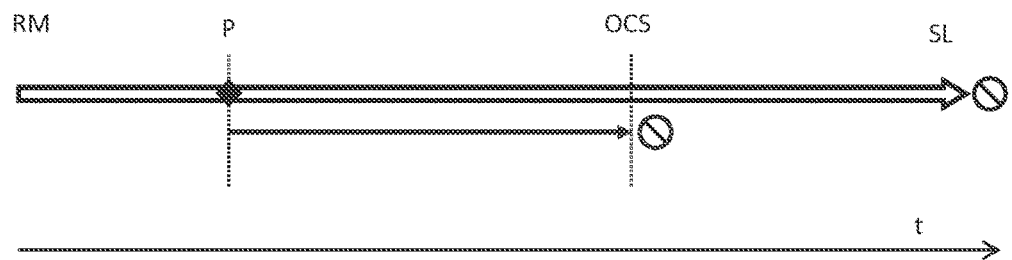
FIG. 11 illustrates schematically how the open container stability time limits reagent usage according to an embodiment of the present disclosure.

FIG. 11 schematically shows how the open container stability time limits reagent usage. In one embodiment, the typical life cycle of a reagent is depicted along line t representing time. RM stands for reagent manufacture; P for reagent container opening (piercing in this case); OCS stands for open container stability time that starts counting from the time the reagent container is opened (P) (typically in hours); SL stands for shelf life that starts counting from the time the reagent is manufactured and closed in a reagent container (RM) (typically in months). The shelf life (SL) can be the maximum time a reagent can be used in an unopened status, assuming that eventual storage conditions are met. As soon as the reagent container is opened (P), the open container stability time OCS can limit the time by when the reagent can be still used.

Figure 12:
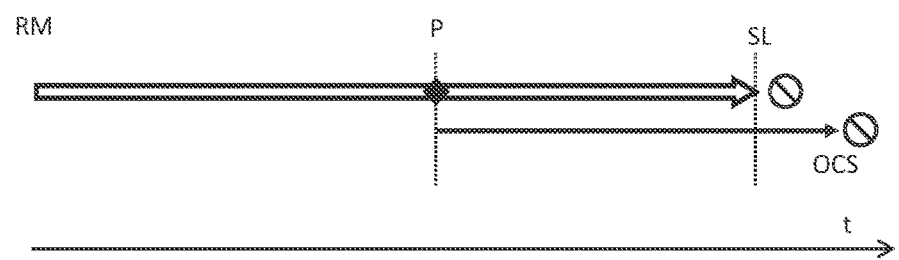
FIG. 12 illustrates schematically how the shelf life limits reagent usage according to an embodiment of the present disclosure.

FIG. 12 schematically illustrates a special case in which a reagent container is opened shortly before its shelf life (SL) expires. In this case, it can be possible that the open container stability time (OCS) would be in theory longer than the shelf life (SL). However, as the reagent cannot be used beyond its shelf life (SL), it can be the shelf life (SL) that, in this case, can limit reagent usage.

The controller 180 can thus keep record of reagent shelf lives (SL) in reagent containers 7, 8, 9 or lots of reagent containers in the reagent container section 112 and of the open container stability times (OCS) by recording the time of opening of the individual reagent containers 7, 8, 9. According to certain embodiments, the controller 180 for each reagent type can instruct the reconstitution device to reconstitute first reagents in those reagent containers 7, 8, 9 or lots with the shortest remaining shelf life (SL) and/or reagents whose shelve life (SL) would otherwise be shorter than the open container stability time (OCS).

Figure 13:
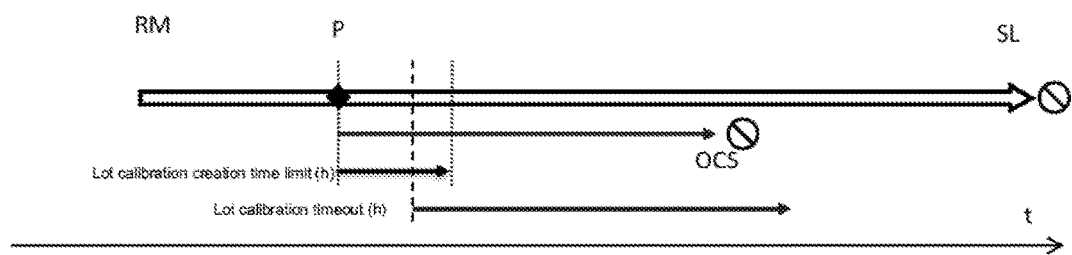
FIG. 13 illustrates schematically a time window for reagent calibration according to an embodiment of the present disclosure.

FIG. 13 schematically shows a time window for reagent calibration. In one embodiment, a lot calibration timeout can be defined that can define how long (in hours) a particular calibration record can be valid for a lot after it has been created. Also, a lot calibration creation time limit can be defined that can define how long (in hours) a reagent can be used for a lot calibration after it has been opened, in view of the open container stability time (OCS). The controller 180 can thus be responsible for keeping record also of these additional time limits and to plan reconstitution also in view of the possibility to run a calibration within the allowed time limit.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A reagent management system, the reagent management system comprising:
   a reagent container section for receiving reagent containers, wherein a reagent container is transported to a reagent container opening position of the reagent container section for opening the reagent container;
   a reagent reconstitution device for reconstituting dry or lyophilized reagents or concentrated liquid reagents provided in the reagent containers in order to carry out in-vitro diagnostic tests with the reconstituted reagents, wherein the reagent container is transported from the reagent container opening position to a reconstitution liquid dispensing position for dispensing a volume of reconstitution liquid into the opened reagent container by the reagent reconstitution device, wherein the reagent container is transported from the reconstitution liquid dispensing position to an agitating position for agitating the reagent container by a reagent container agitating device for reconstituting the dry or lyophilized or concentrated reagent in the reconstitution liquid, wherein the reagent container is transported from the agitating position to a storing position for maintaining the reagent container at rest for a pre-defined time and, optionally, the reagent container is transported from the storing position to the agitating position of the reagent container agitating device for agitating the reagent container for at least a second time;
   a controller that receives information about a number of in-vitro diagnostics tests to be carried out,
   automatically calculates a total volume of reconstituted reagent for any reagent type that is required to carry out the in-vitro diagnostics tests,
   determines if reconstituted reagent that has not yet expired is still available in the reagent container section as well as its remaining open container stability time (OCS), and if a volume of reconstituted reagent of the same reagent type is already available, determines a number of in-vitro diagnostic tests that can be carried out within the remaining open container stability time, and if the number is lower than the number of in-vitro diagnostic tests that have to be carried, the controller calculates an additional volume of reagent of the same type that is required,
   if the reagent containers to be opened in order to obtain the required additional volume have an open container stability time that is insufficient to carry out the in-vitro diagnostic tests, the controller instructs the reagent reconstitution device to open only a limited number of containers and reconstitute only a volume of reagent that can be used within the open container stability time (OCS).

2. The reagent management system according to claim 1, wherein the volume to be reconstituted is manually gettable and the controller is programmed to provide recommendation about the value to be set and/or to warn in case a calculated maximum volume is exceeded or prevent that a calculated maximum volume is exceeded.

3. The reagent management system according to claim 1, wherein the controller is programmed to monitor an available volume of each reagent type, or to calculate how the available volume changes over time and to delay additional reconstitution until the available volume reaches, or drops below a threshold value, or the open container stability time is about to expire.

4. The reagent management system according to claim 1, wherein the calculated volume is reagent type and/or test specific and the controller calculates the volume also according to any one or more of the following rules:
   the shorter the open container stability time (OCS) of the reagent type, the smaller the volume,
   the higher the relative cost of the reagent type, the smaller the volume,
   the lower the frequency of occurring test orders to be carried out with the reagent type, the smaller the volume; and/or
wherein the threshold value is user configurable and/or is reagent type and/or test specific and is set according to any one or more of the following rules:
   the shorter the open container stability time of the reagent type, the lower the threshold value,
   the higher the relative cost of the reagent type, the lower the threshold value,
   the lower the frequency of occurring test orders to be carried out with the reagent type, the lower the threshold value.

5. The reagent management system according to claim 1, wherein the controller is programmed to ask for user confirmation or to check verification of other conditions and/or is reprogrammable in order to take into account user specific time change requests before instructing the reagent reconstitution device to reconstitute additional volume.

6. The reagent management system according to claim 1, wherein the controller is programmed to instruct the reconstitution device to start reconstitution of a reagent type at a pre-defined time preceding an expected number of test orders or within a user configurable timespan or after an initial number of test orders to be carried out with that reagent type is reached.

7. The reagent management system according to claim 1, wherein the controller is programmed to keep record of reagent shelf life (SL) in reagent containers or lots of reagent containers in the reagent container section and for each reagent type to instruct the reconstitution device to reconstitute first reagents in those reagent containers or lots with the shortest remaining shelf life (SL) and/or reagents whose open container stability time (OCS) would otherwise become shorter because close to an end of the shelf life (SL).

8. The reagent management system according to claim 1, wherein the controller is programmed to prioritize reconstitution of those reagent types in those reagent containers or lots that are needed to carry out emergency tests or those that are needed for calibration or control runs, or those that are purposely inserted in a dedicated priority receiving position of the reagent container section.

9. The reagent management system according to claim 1, wherein the reagent reconstitution device comprises,
- a reagent container opener,
- a reconstitution liquid dispenser,
- a liquid mixing device, and
- a reagent container transport device to move reagent containers between any of a reagent container storing position,
- a reconstituted reagent pipetting position,
- an reagent container mixing position, and
- a reagent container inlet/outlet receiving position.

10. The reagent management system according to claim 9, wherein the reconstitution liquid dispenser is a reagent pipetting device adapted to withdraw reconstituted reagent from the same reagent container.

\* \* \* \* \*